United States Patent [19]

Kühlthau et al.

[11] Patent Number: 4,598,151
[45] Date of Patent: Jul. 1, 1986

[54] CATIONIC DYESTUFFS, A PROCESS FOR THEIR PREPARATION, AND THEIR USE FOR DYEING AND MASS-COLORING

[75] Inventors: Hans-Peter Kühlthau, Leverkusen; Horst Harnisch, Much, both of Fed. Rep. of Germany

[73] Assignee: Bayer Aktiengesellschaft, Leverkusen, Fed. Rep. of Germany

[21] Appl. No.: 441,892

[22] Filed: Nov. 15, 1982

[30] Foreign Application Priority Data

Dec. 4, 1981 [DE] Fed. Rep. of Germany ....... 3148104

[51] Int. Cl.[4] ............................................ C07D 209/90
[52] U.S. Cl. .................................... 546/167; 546/165; 546/166; 548/436; 548/438; 548/437; 548/374; 544/142
[58] Field of Search ................ 546/167; 548/436, 438, 548/374, 379; 544/80, 357

[56] References Cited

U.S. PATENT DOCUMENTS

| | | | |
|---|---|---|---|
| Re. 29,834 | 11/1978 | Brack et al. | 548/436 |
| 3,347,865 | 10/1967 | Brack et al. | 548/438 |
| 3,687,972 | 8/1972 | Padmanathan | 548/436 |
| 3,969,346 | 7/1976 | Koller et al. | 548/436 |
| 4,000,141 | 12/1976 | Kuhlthau | 546/167 |
| 4,185,151 | 1/1980 | Kuhlthau | 546/167 |
| 4,283,540 | 8/1981 | Brack | 548/348 |
| 4,446,326 | 5/1984 | Brack | 548/438 |

FOREIGN PATENT DOCUMENTS

2366174 3/1979 Fed. Rep. of Germany .
2921690 12/1980 Fed. Rep. of Germany .

*Primary Examiner*—Glennon H. Hollrah
*Assistant Examiner*—D. L. Dinner
*Attorney, Agent, or Firm*—Sprung Horn Kramer & Woods

[57] ABSTRACT

Dyestuffs of the formula

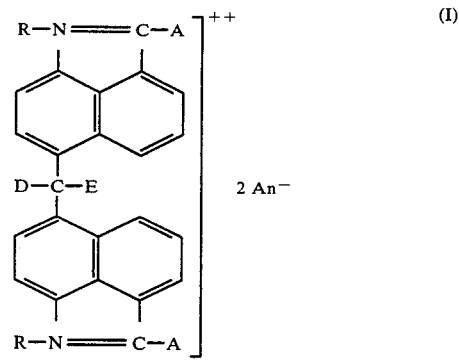

wherein
R represents hydrogen or optionally substituted alkyl,
A represents

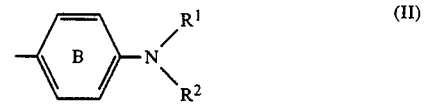

wherein
$R^1$ represents hydrogen, optionally substituted alkyl or cycloalkyl and
$R^2$ represents optionally substituted alkyl which can close a ring to ring B, aralkyl or aryl or
$R^1$ and $R^2$, together with the N atom, form a ring,
D and E represent hydrogen, optionally substituted alkyl or alkenyl and D additionally represents aryl, aralkyl, aralkenyl or a heterocyclic radical, or D and E, together with the C atom, form a ring and
$An^-$ represents an anion, are used for pulp-coloring paper and dyeing cationically dyeable fibres.

3 Claims, No Drawings

CATIONIC DYESTUFFS, A PROCESS FOR THEIR PREPARATION, AND THEIR USE FOR DYEING AND MASS-COLORING

The present invention relates to cationic dyestuffs of the general formula

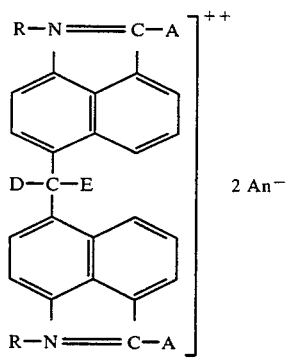

and their bases

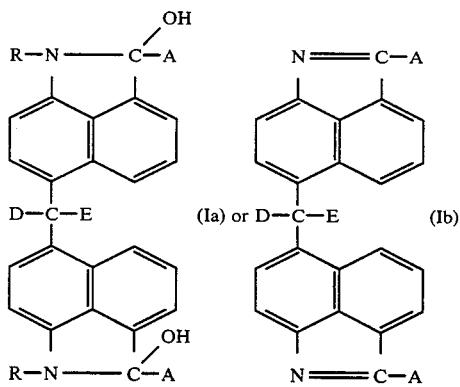

wherein
R represents hydrogen or a $C_1$- to $C_8$-alkyl radical optionally substituted by nonionic radicals,
A represents a radical of the formulae

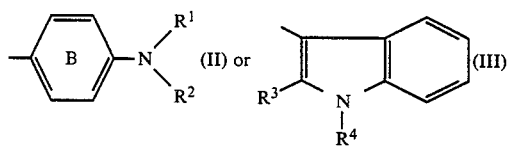

wherein
$R^1$ represents hydrogen, a $C_1$- to $C_6$-alkyl radical optionally substituted by nonionic radicals or cycloalkyl and
$R^2$ represents a $C_1$- to $C_6$-alkyl radical optionally substituted by nonionic radicals and optionally capable of closing a ring to ring B or an aralkyl or aryl radical or
$R^1$ and $R^2$, together with the N atom, form a ring,
$R^3$ denotes a $C_1$- to $C_4$-alkyl radical, a $C_1$- to $C_4$-alkoxycarbonyl radical or an aryl radical,
$R^4$ denotes hydrogen or a $C_1$- to $C_4$-alkyl radical optionally substituted by nonionic radicals, D and E represent hydrogen, a $C_2$- to $C_3$-alkenyl radical or $C_1$- to $C_4$-alkyl radical optionally substituted by nonionic radicals and D additionally represents aryl, aralkyl, aralkenyl or a heterocyclic radical, or D and E, together with the C atom, form a ring, and
$An^-$ represents an anion,
and wherein the rings can contain nonionic radicals customary in dyestuff chemistry, and to a process for preparing these dyestuffs and to their use for pulp-colouring paper and for dyeing cationically dyeable fibres made of polymers and copolymers and acid-modified fibres and polyesters.

Within the scope of this invention possible non-ionic substituents are in particular halogen atoms, nitrile, carboxylate and carboxamide groups, hydroxyl, acyloxy, alkoxy, aralkoxy and aryloxy groups and the analogous mercapto groups, amino groups and amino groups mono- or disubstituted by alkyl, aralkyl, aryl, cycloalkyl or acyl groups, acyl radicals, sulphonamide groups and—on the rings—nitro and alkyl groups, but also carboxyl groups, which dissociate only to a very small extent in the neutral and acid pH range and therefore do not affect the cationic character of the dyestuffs.

Within the scope of the invention an alkyl radical—unless especially indicated—is preferably understood as meaning a radical having 1-4 C atoms.

In particular, aryl represents phenyl and aralkyl represents benzyl or phenylethyl, either of which can in turn be substituted by the nonionic radicals mentioned.

Preferably cycloalkyl is cyclopentyl and cyclohexyl, either of which can be substituted by $C_1$- to $C_4$-alkyl.

Examples of what acyl is understood as meaning are acetyl, propiohyl, benzoyl, $C_1$- to $C_4$-alkylsulphonyl and phenylsulphonyl.

Halogen preferably represents chlorine and bromine.

Suitable heterocyclic ring D belong, for example, to the furan, thiophene, indole, pyridine, pyrimidine or chromenone series.

Dyestuffs to be emphasised have the formula

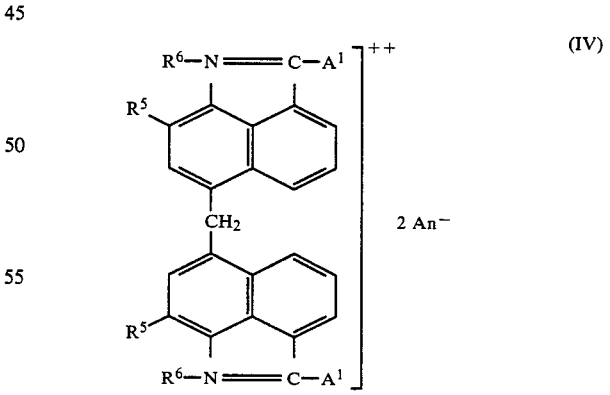

wherein
$R^6$ represents hydrogen, $C_1$- to $C_4$-alkyl which can be substituted by cyano, hydroxyl, $C_1$- to $C_4$-alkoxy, chlorine, $C_1$- to $C_4$-alkoxycarbonyl, aminocarbonyl or mono- or di-$C_1$- to $C_4$-alkylaminocarbonyl,
$R^5$ represents hydrogen, chlorine or bromine,
$A^1$ represents

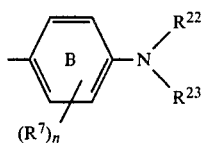

(V)

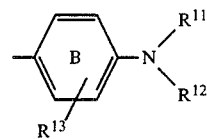

(VII)

wherein $R^{22}$ denotes hydrogen or a $C_1$- to $C_6$-alkyl radical optionally substituted by 1–3 hydroxyl, 1–3 halogen, $C_1$- to $C_4$-alkoxy, cyano, $C_1$- to $C_4$-alkylcarbonyloxy, hydroxy-$C_1$- to $C_4$-alkoxy, aminocarbonyl, carboxyl, $C_1$- to $C_4$-alkoxycarbonyl or $C_3$- or $C_4$-alkenyloxy, by acyloxy, benzyloxy, phenyloxy, sulphonamido or acylamido, a $C_2$- to $C_4$-alkenyl radical optionally substituted by halogen or a cyclohexyl radical optionally substituted by $C_1$- to $C_4$-alkyl radical, $R^{23}$ denotes a $C_1$- to $C_6$-alkyl radical optionally substituted like $R^{22}$, benzyl or phenyl, or, together with the ring B, a tetrahydroquinoline, indoline, hexahydrocarbazole or dihydrobenzoxazine, all of which can carry $C_1$- to $C_4$-alkyl and phenyl groups, or $R^{22}$ and $R^{23}$ together denote a pyrrolidine, piperidine, morpholine, pyrazoline or piperazine ring, all of which can carry $C_1$- to $C_4$-alkyl and phenyl groups, $R^7$ denotes $C_1$- to $C_4$-alkyl, $C_1$- to $C_4$-alkoxy or halogen and n denotes 1 to 4, or $A^1$ represents

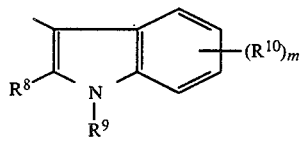

(VI)

wherein $R^8$ denotes an alkyl radical having 1 to 4 C atoms, a phenyl radical or an alkoxycarbonyl radical having 1 to 4 C atoms, $R^9$ denotes hydrogen, an alkyl radical having 1 to 4 C atoms and optionally substituted by hydroxyl, halogen, alkoxy having 1 to 4 C atoms, cyano or acyloxy and $R^{10}$ denotes hydrogen, halogen, $C_1$- to $C_4$-alkyl, $C_1$- to $C_4$-alkoxy, carbalkoxy having 1 to 4 C atoms, $C_1$- to $C_4$-alkylsulphonyl, phenylsulphonyl, acetyl or benzoyl and m denotes 1 to 4, and $An^-$ represents an anion, and wherein the phenyl radicals can be substituted by $C_1$- to $C_4$-alkyl, $C_1$- to $C_4$-alkoxy, hydroxyl, chlorine or bromine.

Among dyestuffs of the formula IV, those are preferable wherein $R^6$ represents hydrogen, $C_1$- to $C_4$-alkyl, $\beta$-cyanoethyl, $\beta$-hydroxyethyl, $\beta$-alkoxyethyl, $\beta$-chloroethyl, methoxycarbonylmethyl or ethoxycarbonylmethyl, $R^5$ represents hydrogen and $A^1$ represents wherein $R^{11}$ denotes hydrogen or a $C_1$- to $C_4$-alkyl radical optionally substituted by hydroxyl, methoxy, ethoxy, chlorine, cyano, acetoxy or acetyl, $R^{12}$ denotes a $C_1$- to $C_4$-alkyl radical optionally substituted by hydroxyl, methoxy, ethoxy, chlorine, cyano, acetoxy or acetyl, benzyl or phenyl optionally substituted by chlorine, methyl, methoxy or ethoxy, $R^{13}$ denotes hydrogen, methyl, chlorine, methoxy or ethoxy, $A^1$ represents

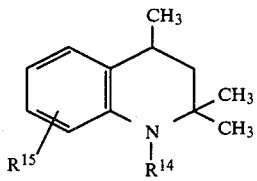

(VIII)

wherein $R^{14}$ denotes hydrogen or $C_1$- to $C_4$-alkyl, $C_2$- to $C_4$-hydroxyalkyl, chloroethyl, bromoethyl, methoxyethyl, cyanoethyl, acetoxyethyl, hydroxyethoxyethyl, aminocarbonylethyl, carboxyethyl, $\gamma$-cyanopropyl, $\beta$-hydroxy-$\gamma$-allyloxy-n-propy, $\beta$-hydroxy-$\gamma$-methoxy-n-propyl, $\beta$-hydroxy-$\gamma$-ethoxy-n-propyl, $\beta$-hydroxy-$\gamma$-butoxy-n-propyl, $\beta$-chloro-n-propyl, $\beta$-chloro-n-butyl, $\beta$-chloro-i-butyl, $\beta,\gamma$-dichloro-n-propyl, $\beta$-acetoxy-n-propyl, $\beta$-hydroxy-$\gamma$-chloro-n-propyl, vinyl, allyl, methallyl, chloroallyl or cyclohexyl and $R^{15}$ denotes hydrogen, methoxy or ethoxy, or $A^1$ represents (IX)

wherein $R^{16}$ denotes methyl or phenyl optionally substituted by chlorine, methyl or methoxy and $R^{17}$ denotes a $C_1$- to $C_4$-alkyl radical optionally substituted by hydroxyl, chlorine, cyano or acyloxy or hydrogen.

Particularly preferable dyestuffs are of the general formula

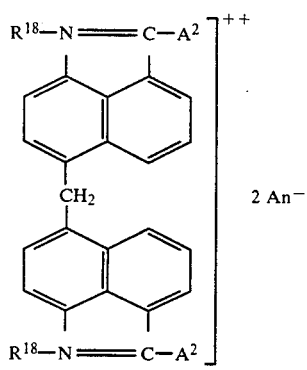 (X)

wherein

R$^{18}$ represents methyl, ethyl or β-cyanoethyl and A$^2$ represents

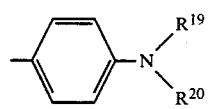 (XI)

wherein

R$^{19}$ denotes hydrogen, methyl, ethyl, cyanoethyl, hydroxyethyl, acetoxyethyl, methoxyethyl, ethoxyethyl, chloroethyl, hydroxypropyl, propyl or butyl and R$^{20}$ denotes one of the alkyl groups mentioned for R$^{19}$ or phenyl, methoxyphenyl, ethoxyphenyl, methylphenyl or chlorophenyl, or A$^2$ very particularly preferably represents

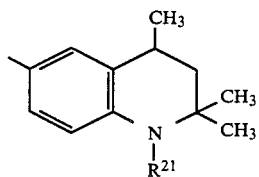 (XII)

wherein

R$^{21}$ denotes hydrogen, methyl, ethyl, propyl, butyl, hydroxyethyl, hydroxypropyl, cyanoethyl, chloroethyl, acetoxyethyl, acetoxypropyl, methoxyethyl, ethoxyethyl, hydroxybutyl, hydroxycarbonylethyl or hydroxyethoxyethyl and An$^-$ represents an anion.

The new dyestuffs are prepared by condensing a naphtholactam derivative of the formula

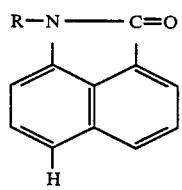 (XIII)

wherein

R has the abovementioned meaning and the naphtholactam rings can be substituted as indicated in the formula (I)

with a compound of the formula

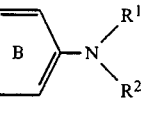 (XIV)

or

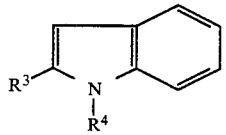 (XV)

in either of which

R$^1$, R$^2$, B, R$^3$ and R$^4$ have the meanings indicated for the formulae II and III and the rings can contain the substituents indicated in the forulae I, II and III and with a compound of the formula

 (XVI)

wherein

D and E have the meaning indicated in the formula (I)

in any order.

The condensation with (XIV) or (XV) is most advantageously carried out in phosphorus oxychloride with the addition of phosphorus pentoxide at temperatures between about 35° C. and the boiling point of the mixture.

The subsequent condensation with (XVI) or the reaction of (XIII) with (XVI) in a molar ratio of 2:1 is advantageously carried out in 65–96% strength sulphuric acid or in mixtures of glacial acetic acid and sulphuric acid within a temperature range of 20°–120° C.

The new dyestuffs have a very high affinity for cellulose, which also makes possible the colouring of lignin-free bleached wood pulps with almost quantitative dyestuff take-up. The effluents obtained accordingly contain no or almost no dyestuff. The dyeings are distinguished by good light fastness values.

The dyestuffs are also suitable for dyeing, printing and spin-dyeing materials which predominantly or completely consist of polyacrylonitrile or its copoymers with other vinyl monomers, such as vinylidene cyanide, vinylidene chloride, vinyl chloride, vinyl acetate, vinyl alcohol, acrylates or methacrylates or of acid-modified polyesters or polyamides. The dyeings and prints obtained are distinguished by good all round fastness properties, in particular by high light, wet and prespiration fastness properties, by a high affinity for the fibre, and by a high pH stability.

Although the dyestuffs according to the invention are readily soluble in water, they do not bleed at all, or only to a very small extent, in the bleed test on spun-dyed polyacrylonitrile fibres. They are therefore excellently suitable for spin-dyeing polyacrylonitrile or its copolymers. The dyestuffs according to the invention are readily soluble in the solvents used for spinning, when the dyestuffs are present as customary salts of inorganic or organic acids, for example as chloride, sulphate, acetate or lactate. The solubility can be increased by converting the dyestuff salts into salts of polynuclear aromatic sulphonic acids. The dyestuffs are also highly suitable for spin-dyeing in the form of their bases of the formulae Ia or Ib.

The invention also relates to naphtholactam derivatives of the formula

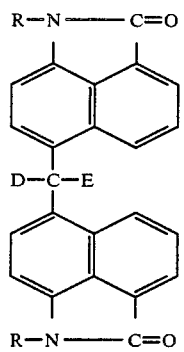

(XVII)

wherein

R, D and E have the abovementioned meaning and the naphthalene ring can be substituted in the manner described and to their preparation from compounds (XIII) and (XVI), in particular formaldehyde.

The formaldehyde is most advantageously present as paraformaldehyde.

Examples of other suitable carbonyl compounds (XVI) are acetaldehyde, trichloroacetaldehyde, butan-1-al, acrolein, cinnamaldehyde, hydrocinnamaldehyde, benzaldehyde, o-chlorobenzaldehyde, p-chlorobenzaldehyde, p-tolylaldehyde, chromenon-3-aldehyde, thiophen-2-aldehyde, indol-3-aldehyde, pyridin-3-aldehyde, acetone and cyclohexanone.

Examples of suitable compounds of the formula (XIII) are the naphtholactam derivatives mentioned in U.S. Pat. No. 4,000,141 and in German Offenlegungsschrift No. 2,557,503 and unsubstituted in the p-position relative to the nitrogen.

By chlorinating or brominating condensation products prepared from (XIII) and (XVI), further compounds of the formula (XVII) are obtained.

Examples of suitable compounds of the formula (XIV) are the tetrahydroquinolines mentioned in U.S. Pat. No. 4,000,141 and in German Offenlegungsschrift 2,557,503 and the coupling components listed in U.S. Pat. No. 4,051,084 and in German Offenlegungsschrift Nos. 2,255,058, 2,255,059, 2,255,060, 2,344,672, 2,344,735 and 2,344,901.

Possible examples of anions An⁻ are the anions enumerated in German Offenlegungsschrift No. 2,255,058.

EXAMPLE 1

81.3 g of the naphtholactam derivative of the formula

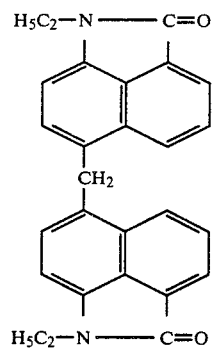

108.7 g of N-β-acetoxyethyl-2,2,4-trimethyltetrahydroquinoline and 150 g of phosphorus oxychloride are stirred together, 25 g of phoshorus pentoxide are added to the mixture, and the batch is maintained for 12 hours at 75° C. The melt is then stirred into 1 liter of water at 45° C., and the solution obtained is heated to the boil. After the solution has been cooled down, the dyestuff obtained crystallises out. It is filtered off with suction, dissolved in 1.5 liters of hot water, clarified with 20 g of active charcoal and then re-precipitated with evaporated salt. The crystalline dyestuff is filtered off with suction and dried in vacuo. It has the formula

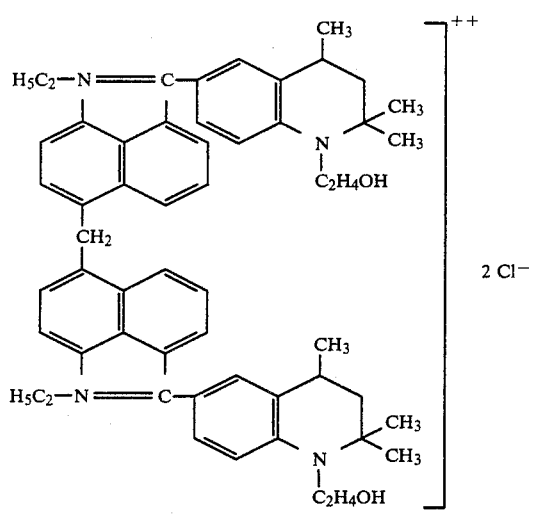

and dyes Dralon blue in the exhaust method (C.I. hue indication chart No. 14).

EXAMPLE 2

30 g of the dyestuff described in Example 1 are dissolved in 270 g of dimethylformamide. This solution is introduced immediately before spinning by means of a metering pump into a solution of 3 kg of acid-modified polyacrylonitrile in dimethylformamide, and the homogenised solution is then spun using a customary dry-spinning process. Intensely reddish-tinged blue filaments are obtained which are distinguished by excellent fastness properties, in particular light, rubbing, wet and steaming fastness properties.

In the fibre is prepared using a customary wet-spinning process, a similarly good result is obtained. The coagulation and stretching baths are not coloured, because the dyestuff does not bleed.

EXAMPLE 3

40.6 g of the naphtholactam derivative used in Example 1, 44.7 g of N-ethyl-2,2,4-trimethyltetrahydroquinoline and 75 g of $POCl_3$ are mixed with one another, 12.5 g of phosphorus pentoxide are added to the mixture, and the batch is stirred for 12 hours at 75° C. The melt is then stirred into 500 ml of water, and the mixture is stirred until the $POCl_3$ decomposes and the dyestuff is crystalline. It is filtered off with suction and dried in vacuo. Its structure corresponds to the formula

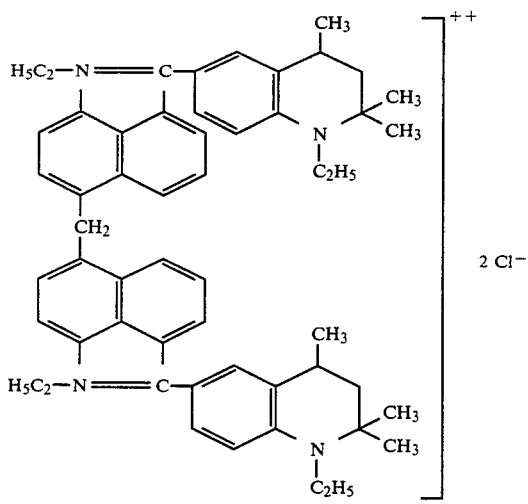

If this dyestuff is used as described in Example 2 for spin-dyeing, blue filaments having excellent fastness properties are likewise obtained. The exhaust method produces on Dralon a greenish-tinged blue (C. I. hue indication chart No. 15).

EXAMPLE 4

A dry stuff consisting of bleached sulphite pulp is beaten with water and milled to a degree of freeness of 40° Schopper-Riegler in a Hollander, so that the solids content is slightly above 2.5%, and the solids content of the slush pulp is then adjusted with water to exactly 2.5%. 5 g of an 0.25% strength aqueous solution of the dyestuff in accordance with Example 3 are added to 200 g of this slush pulp, and the mixture is stirred for about 5 minutes and processed, without the addition of resin size and alum, to give paper. Sheet paper coloured in a deep blue shade is obtained. According to photometric determination, the effluent contains only about 1% of the dyestuff employed. If the pulp-colouring of paper is carried out in the presence of 2% of resin size and 4% alum, a similar result is obtained.

A blue paper colouring of a desired neutral blue shade is obtained, when the colouring is carried out with C.I. Basic Blue 140 to which, relative to the active ingredient, 10% of the dyestuff of Example 3 has been added.

If the dyestuff of Example 1 is used instead of the dyestuff of Example 3 and the procedure described in Example 4 is followed, likewise good results are obtained.

EXAMPLE 5

40.6 g of the naphtholactam derivative used in Example 1, 38.5 g of 2,2,4-trimethyltetrahydroquinoline and 95 g of $POCl_3$ are stirred with one another at room temperature, 12.5 g of $P_2O_5$ are added to the mixture, and condensation is carried out for 12 hours at 70° C. The melt is then stirred into 500 ml of water. The dyestuff is filtered of with suction, when all the phosphorus oxychloride has decomposed. The dyestuff corresponds to the formula

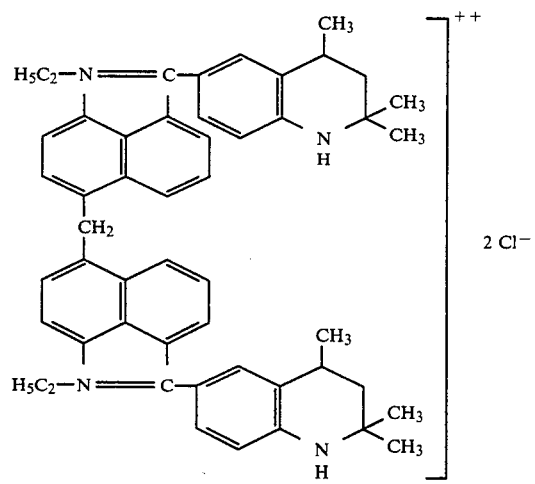

If the dyestuff is used for spin-dyeing in a manner analogous to the procedure described in Example 2, blue filaments are obtained which have very good fastness properties.

A blue colouring is obtained when the dyestuff is used as a paper dyestuff in accordance with Example 4.

The dyestuff dyes polyacrylonitrile greenish-tinged blue in the exhaust method (hue indication chart No. 15).

EXAMPLE 6

8 g of the naphtholactam derivative shown by its formula in Example 1 are stirred together with 10 g of diethylaniline, 30 g of $POCl_3$ and 7 g of $P_2O_5$ for 15 hours at 40° C. After the melt has been decomposed with water, the dyestuff is precipitated with sodium chloride, filtered off with suction, dissolved hot in water, clarified with 3 g of active charcoal and re-precipitated with evaporated salt. It is filtered off with suction and dried in vacuo. The dyestuff obtained corresponds to the formula

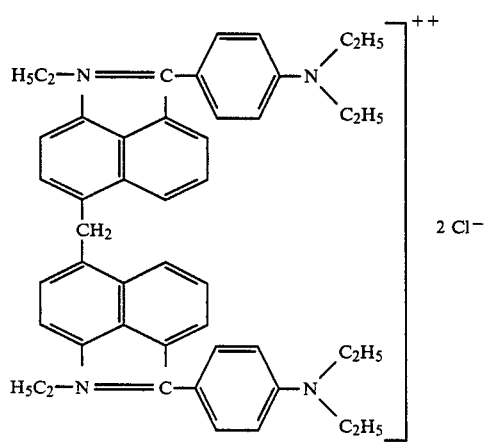

and is highly suitable for preparing reddish-tinged blue spun-dyed filaments analogously to Example 2.

Polyacrylonitrile is dyed blue by the dyestuff in the exhaust method (C. I. hue indication chart No. 14).

EXAMPLE 7

4 g of the naphtholactam derivative used in Example 1, 6 g of β-acetoxyethyloxyethyl-Nβ-acetoxyethyldiphenylamine, 25 g of POCl₃ and 5 g of P₂O₅ are condensed for 15 hours at 40° C. The melt is decomposed with water, the mixture is heated to the boil, and after cooling down the dyestuff crystallised out is filtered off with suction and dried. It has the formula:

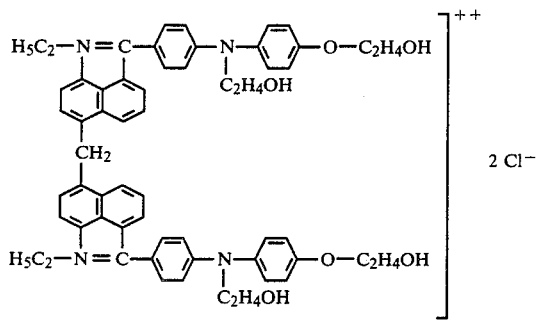

If the dyestuff is used analogously to Example 2 for spin-dyeing polyacrylonitrile, reddish-tinged blue filaments having excellent fastness properties are obtained.

If polyacrylonitrile fabric is dyed with the dyestuff described above using a customary exhaust method, a reddish-tinged blue dyeing having excellent light fastness is obtained (C. I. hue indication chart No. 13).

Paper is also coloured blue by this dyestuff.

EXAMPLE 8

8 g of the naphtholactam derivative used in Example 1 are condensed at 80° C. with 6 g of 2-methyl-indole in 25 g of phosphorus oxychloride. After the melt has been decomposed with water and the product has been precipitated with evaporated salt, the dyestuff of the formula:

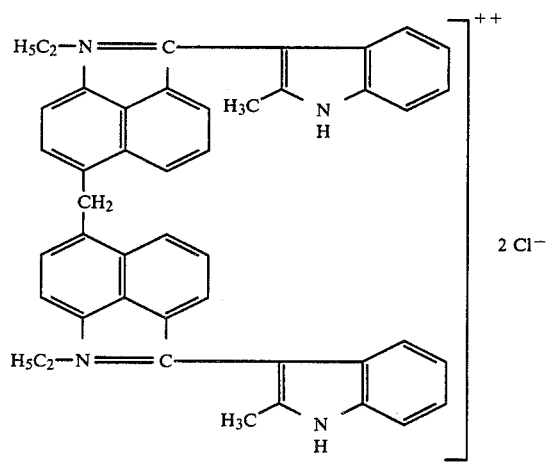

is obtained. It dyes/colours acid-modified synthetic fibres and paper bluish-tinged violet (C.I. hue indication chart No. 12).

EXAMPLE 9

The procedure described in Example 1 is followed, but the dyestuff is precipitated from the clarified hot solution not by means of evaporated salt, but by the dropwise addition of a 40% strength solution of the ammonium salt of the condensation product of formaldehyde and 4,4'-dihydroxydiphenyl sulphone containing sulphonic acid groups until all of the dyestuff salt has precipitated. A blue powder is obtained which is insoluble in water and which, after filtering off with suction, washing with water and drying, it highly suitable for spin-dyeing, for example analogously to the process given in Example 2. The same result as in Example 2 is obtained.

The dyestuffs mentioned in Examples 3, 5, 6, 7 and 8 can be isolated from their aqueous solutions, possibly clarified with active charcoal, in the same way as water-insoluble salts of the condensation product of formaldehyde and sulpho-containing 4,4'-dihydroxydiphenyl sulphone which are excellently suitable for spin-dyeing.

If the salts which are sparingly soluble in water are dissolved in dimethylformamide which contains 10% of acetic acid, the following maxima are obtained within the visible region:

Dyestuff of Example 1: 618 nm
Dyestuff of Example 3: 620 nm
Dyestuff of Example 5: 608 nm.

EXAMPLE 10

The procedure described in Example 1 is followed, but the dyestuff is precipitated from the clarified, cooled-down solution not by means of evaporated salt but by the dropwise addition of sodium hydroxide solution until all of the carbinol base of the formula

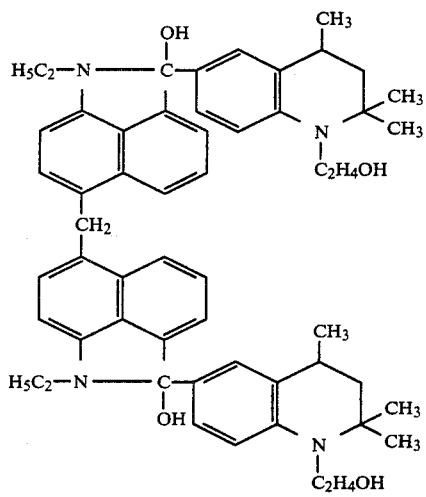

has precipitated. After filtering off with suction, washing with water and drying, the base is excellently suitable for spin-dyeing analogously to the process given in Example 2. The same result as in Example 2 is obtained.

The carbinol bases of the dyestuffs mentioned in Examples 3, 5, 6, 7 and 8 are also highly suitable for spin-dyeing.

For example, also the following dyestuffs can be prepared analogously to the procedure given in the above examples. The dyestuffs produce on paper or as spin-dyestuffs also in the form of their carbinol bases or as precipitation products with polynuclear sulphonic acids dyeings in the shades indicated in the table below.

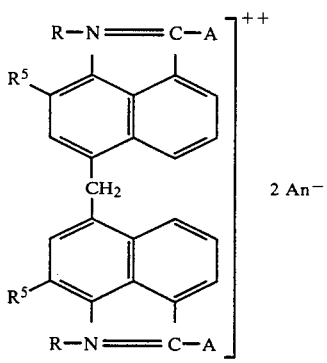

| Example | R | A | R⁵ | Colouring of paper | H.I.C.No.* | Spin-dyeing of PAC |
|---|---|---|---|---|---|---|
| 11 | $C_2H_5$ | ![p-dimethylaminophenyl] | H | blue | 13 | reddish-tinged blue |
| 12 | $CH_3$ | ![1-ethyl-2,2,4-trimethyl-tetrahydroquinolin-6-yl] | H | " | 14 | blue |
| 13 | $C_2H_5$ | " | Cl | " | 15 | " |
| 14 | " | ![1-(2-hydroxyethyl)-2,2,4-trimethyl-tetrahydroquinolin-6-yl] | Br | " | 15 | " |
| 15 | $C_2H_4CN$ | ![1-ethyl-2,2,4-trimethyl-tetrahydroquinolin-6-yl] | H | reddish-tinged blue | 13 | reddish-tinged blue |
| 16 | $C_2H_4OH$ | " | " | reddish-tinged blue | 13 | reddish-tinged blue |
| 17 | $-CH_2-COOCH_3$ | " | " | blue | 13 | reddish-tinged blue |
| 18 | $C_4H_9$ | " | " | " | 15 | blue |
| 19 | $C_2H_4OCH_3$ | " | " | " | 14 | " |
| 20 | $-CH_2-CH=CH_2$ | " | " | " | 15 | " |
| 21 | $C_2H_5$ | ![1-butyl-2,2,4-trimethyl-tetrahydroquinolin-6-yl] | " | " | " | " |

-continued

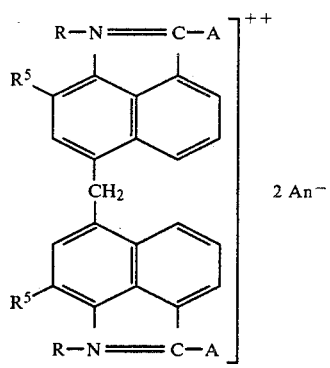

| Example | R | A | R⁵ | Colouring of paper | H.I.C.No.* | Spin-dyeing of PAC |
|---|---|---|---|---|---|---|
| 22 | " | —⟨⟩—NH—⟨⟩ | " | " | 13 | reddish-tinged blue |
| 23 | " | —⟨⟩—N(N=C(CH₃)CH₂CH₂) | " | " | 14 | blue |
| 24 | " | —⟨⟩—N(morpholine) | " | " | 13 | reddish-tinged blue |
| 25 | " | 2,3-dimethyl-1-methylindol-5-yl | " | violet | 12 | bluish-tinged violet |
| 26 | " | 1,2,2,4-tetramethyl-1,2,3,4-tetrahydroquinolin-6-yl | " | blue | 14 | blue |
| 27 | " | 1-(2-hydroxypropyl)-2,2,4-trimethyl-1,2,3,4-tetrahydroquinolin-6-yl | " | " | 15 | " |
| 28 | " | 8-methoxy-2,2,4-trimethyl-1,2,3,4-tetrahydroquinolin-6-yl | " | " | 15 | " |

-continued

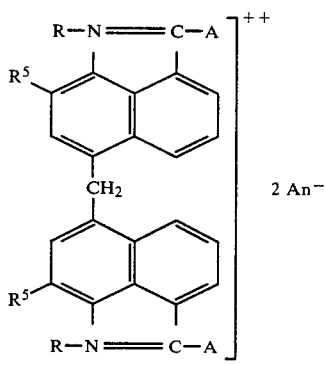

2 An⁻

| Example | R | A | $R^5$ | Colouring of paper | H.I.C.No.* | Spin-dyeing of PAC |
|---|---|---|---|---|---|---|
| 29 | " | (structure: tetrahydroquinoline with CH₃, CH₃, CH₃, N-H, OC₂H₅) | " | " | 15 | " |
| 30 | " | (structure: tetrahydroquinoline with CH₃, CH₃, CH₃, N-C₂H₄Cl) | " | " | 14 | " |
| 31 | " | (structure: tetrahydroquinoline with CH₃, CH₃, CH₃, OCH₃, N-CH₂-CHCl-CH₃) | " | " | 16 | greenish-tinged blue |
| 32 | " | (structure: indoline with CH₃, N-cyclohexyl, H) | " | " | 13 | reddish-tinged blue |

*C.I. hue indication chart No. when dyeing polyacrylonitrile using the exhaust method

EXAMPLE 33

394 g of N-ethylnaphtholactam are suspended in 2 liters of glacial acetic acid, and 36 g of paraformaldehyde are added to the suspension, and 200 ml of concentrated sulphuric acid are added dropwise with cooling at 20°–25° C. The mixture is then stirred at this temperature for 2–3 hours, and the precipitate is filtered off with suction. The filter cake is then stirred into 1,200 ml of methanol, filtered off with suction, washed with methanol and dried at 50° C. in vacuo. 391.9 g of methylene-bis-naphtholactam of the formula:

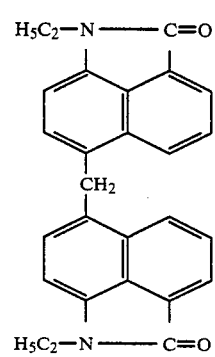

corresponding to 96.5% of theory, are obtained. Melting point 262° C.; m/e=406 (M⊕).

If the dyestuffs of the examples which follow are dissolved in a mixture of ⅔ of methanol and ⅓ of 20% strength acetic acid, the following maxima are measured in the visible region:

| Dyestuff of Example | max (nm) |
|---|---|
| 1 | 618 |
| 5 | 606 |
| 6 | 606 |
| 7 | 588 |
| 8 | 546 |
| 11 | 594 |
| 22 | 584 |
| 23 | 612 |
| 25 | 552 |

EXAMPLE 34

197 g of N-ethyl-naphtholactam are added to 1,700 g of 78% strength sulphuric acid, 74 g of benzaldehyde are added, and the mixture is heated for 7 hours at 100° C. After the solution has been cooled down to 25° C. it is added to 5 liters of ice-water. After stirring for 1 hour, the crystalline precipitate is filtered off with suction, washed with water, stirred for 30 minutes with 5 liters of water and sufficient 50% strength sodium hydroxide solution for the suspension to have a weakly alkaline reaction, washed again with water and dried in vacuo at 60° C. 232 g of a compound of the formula

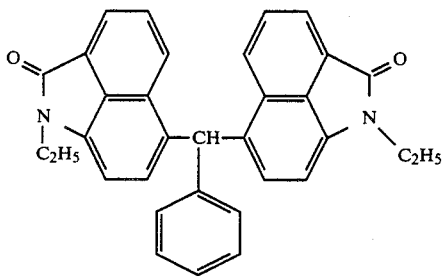

are obtained. Melting point: 274°–275° C.; m/e=482 (M⊕).

Analogous bis-naphtholactam compounds are obtained by using equivalent amounts of one of the following aldehydes instead of benzaldehyde (melting point of the particular bis-naphtholactam in brackets): 2-chlorobenzaldehyde (178° C.), 4-chlorobenzaldehyde (270° C.), 4-tolylaldehyde (157° C.), hydrocinnamaldehyde (182° C.), chromen-4-on-3-aldehyde (270° C.), and also pyridin-4-aldehyde, furfural, thiophen-2-aldehyde, butan-1-al and 4-methoxybenzaldehyde.

EXAMPLE 35

24.2 g of the naphtholactam derivative described in Example 34 and 22.5 g of N-ethyl-2,2,4-trimethyltetrahydroquinoline are stirred in 40 g of phosphorus oxychloride, 7 g of phosphorus pentoxide are added to the mixture, and condensation is then carried out for 12 hours at 75° C. The melt is then stirred into 500 ml of water, the mixture is stirred until the dyestuff is crystalline, and the solids are filtered off with suction and dried in vacuo at 50° C. The product obtained has the formula

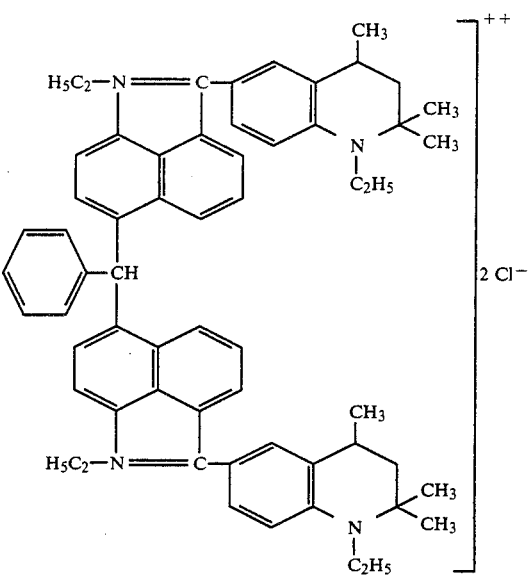

It colours paper in a brilliant blue. The dyeing on polyacrylonitrile corresponds to C.I. hue indication chart No. 14.

EXAMPLE 36

The initial procedure followed is as in Example 35, but N-ethyl-2,2,4-trimethyltetrahydroquinoline is replaced by the equivalent amount of N-β-acetoxyethyl-2,2,4-trimethyltetrahydroquinoline. After the condensation is complete, the melt is stirred into 350 ml of water at 45° C., the mixture is heated to the boil, and the dyestuff obtained is filtered off after the mixture has cooled down. The dyestuff is dissolved in dilute acetic acid, clarified with active charcoal and re-precipitated with evaporated salt. The dyestuff corresponds to the formula

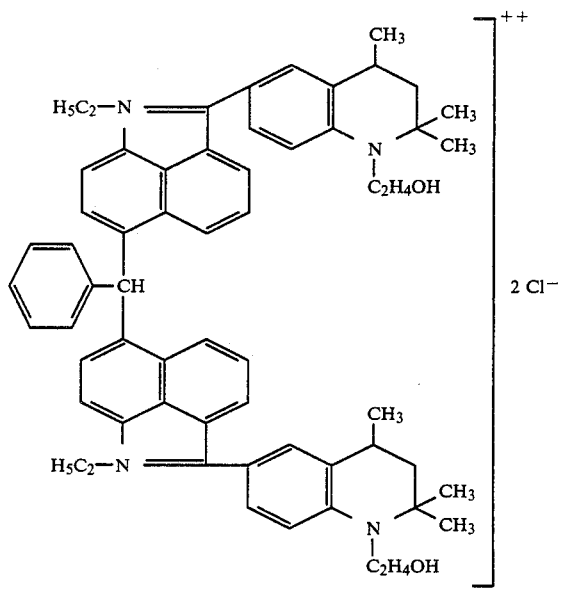

It colours paper in a brilliant blue. The dyeing on polyacrylonitrile corresponds to C. I. hue indication chart No. 14.

If the following naphtholactam derivatives of the formula XVII and tetrahydroquinolines of the formula XII are reacted with one another analogously to Examples 34 and 35, the dyestuffs listed in the table below and of the formula

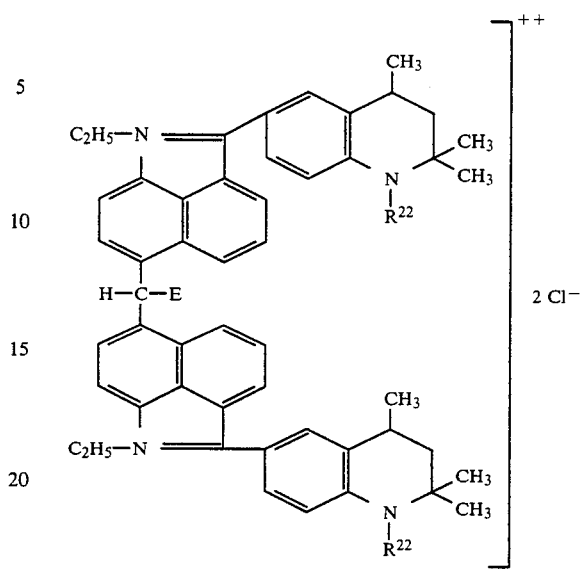

are obtained.

TABLE

| Example | E | $R^{21}$ | $R^{22}$ | Colour on paper | Hue. Ind. Chart on polyacrylonitrile |
|---------|---|----------|----------|-----------------|--------------------------------------|
| 36 | 2-Cl-C6H4- | C2H4OCOCH3 | C2H4OH | brilliant blue | 14 |
| 37 | " | C2H5 | C2H5 | brilliant blue | 15 |
| 38 | chromone | C2H4OCOCH3 | C2H4OH | blue | 16 |
| 39 | " | C2H5 | C2H5 | blue | 17 |
| 40 | 4-Cl-C6H4- | C2H4OCOCH3 | C2H4OH | blue | 14 |
| 41 | -CH2CH2-C6H5 | " | " | blue | 14 |
| 42 | 3,4-di-Cl-C6H3- | C2H5 | C2H5 | blue | 15 |
| 43 | " | C2H4OCOCH3 | C2H4OH | blue | 15 |

TABLE-continued

| Example | E | $R^{21}$ | $R^{22}$ | Colour on paper | Hue. Ind. Chart on polyacrylonitrile |
|---|---|---|---|---|---|
| 44 | 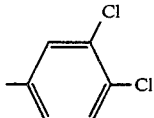 | $C_2H_5$ | $C_2H_5$ | blue | 46 |
| 45 | " | $C_2H_4OCOCH_3$ | $C_2H_4OH$ | blue | 15 |
| 46 | 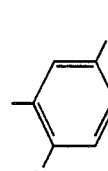 | $C_2H_5$ | $C_2H_5$ | blue | 15 |
| 47 | " | $C_2H_4OCOCH_3$ | $C_2H_4OH$ | blue | 15 |

We claim:

1. A cationic dyestuff of the formula

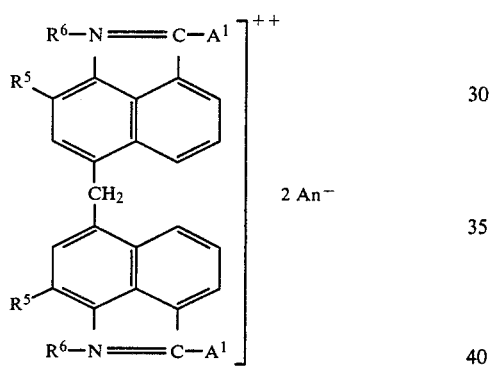

wherein
$R^6$ represents hydrogen, $C_1$- to $C_4$-alkyl optionally substituted by cyano, hydroxyl, or chlorine,
$R^5$ represents hydrogen, chlorine or bromine,
$A^1$ represents

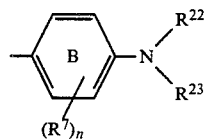

wherein
$R^{22}$ denotes hydrogen or $C_1$- to $C_6$-alkyl optionally substituted by 1-3 hydroxyl, 1-3 -halogen, or cyano,
$R^{23}$ denotes $C_1$- to $C_6$-alkyl optionally substituted like $R^{22}$, benzyl or phenyl, or, together with the ring B, tetrahydroquinoline, optionally substituted by $C_1$- to $C_4$-alkyl groups,
$R^7$ denotes $C_1$- to $C_4$-alkyl, $C_1$- to $C_4$-alkoxy or halogen and
n denotes 1 to 4, and
$An^-$ represents an anion.

2. A dyestuff according to claim 1, wherein
$R^6$ represents $C_1$- to $C_4$-alkyl, $\beta$-cyanoethyl, $\beta$-hydroxyethyl,
$R^5$ represents hydrogen and
$A^1$ represents

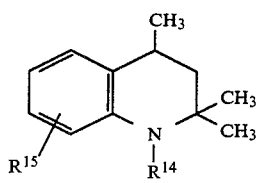

wherein
$R^{11}$ denotes hydrogen or a $C_1$- to $C_4$-alkyl radical optionally substituted by hydroxyl, chlorine, cyano,
$R^{12}$ denotes a $C_1$- to $C_4$-alkyl radical optionally substituted by hydroxyl, chlorine, or cyano, benzyl or phenyl optionally substituted by chlorine, methyl, methoxy or ethoxy,
$R^{13}$ denotes hydrogen, methyl, chlorine, methoxy or ethoxy,
$A^1$ represents wherein
$R^{14}$ denotes hydrogen or $C_1$- to $C_4$-alkyl, $C_2$- to $C_4$-hydroxyalkyl, chloroethyl, cyanoethyl, and
$R^{15}$ denotes hydrogen, methoxy or ethoxy.

3. A dyestuff of the formula

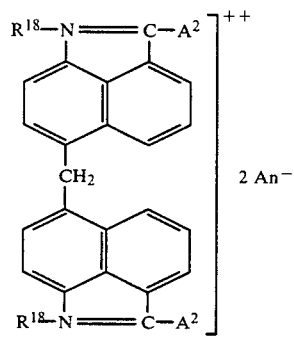

wherein

R[18] represents methyl, ethyl or β-cyanoethyl and

A[2] represents

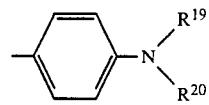

wherein
R[19] denotes hydrogen, methyl, ethyl, cyanoethyl, hydroxyethyl, chloroethyl, hydroxypropyl, propyl or butyl and
R[20] denotes one of the alkyl groups mentioned for R[19] or phenyl, methoxyphenyl, ethoxyphenyl, methylphenyl or chlorophenyl, or
A[2] represents

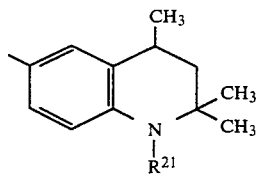

wherein
R[21] denotes hydrogen, $C_1$- to $C_4$-alkyl, hydroxyethyl, hydroxypropyl, cyanoethyl, chloroethyl, hydroxybutyl, and
An⁻ represents an anion.

* * * * *